United States Patent
MacDougall et al.

(10) Patent No.: US 10,687,738 B2
(45) Date of Patent: Jun. 23, 2020

(54) SYSTEMS AND METHODS FOR PERFORMING PHASE-SENSITIVE ACOUSTIC VIBRATIONS USING OPTICAL COHERENCE TOMOGRAPHY

(71) Applicant: AUDIOPTICS MEDICAL INCORPORATED, Halifax, NS (CA)

(72) Inventors: Daniel MacDougall, Dartmouth (CA); Robert Adamson, Halifax (CA)

(73) Assignee: AUDIOPTICS MEDICAL INCORPORATED, Halifax, NS (CA)

(*) Notice: Subject to any disclaimer, the term of this patent is extended or adjusted under 35 U.S.C. 154(b) by 0 days.

(21) Appl. No.: 16/488,406

(22) PCT Filed: Feb. 22, 2018

(86) PCT No.: PCT/CA2018/050200
§ 371 (c)(1),
(2) Date: Aug. 23, 2019

(87) PCT Pub. No.: WO2018/152632
PCT Pub. Date: Aug. 30, 2018

(65) Prior Publication Data
US 2020/0060583 A1    Feb. 27, 2020

Related U.S. Application Data

(60) Provisional application No. 62/463,298, filed on Feb. 24, 2017.

(51) Int. Cl.
*A61B 5/12* (2006.01)
*G01B 9/02* (2006.01)
*A61B 5/00* (2006.01)

(52) U.S. Cl.
CPC ............ *A61B 5/126* (2013.01); *A61B 5/0051* (2013.01); *A61B 5/0066* (2013.01);
(Continued)

(58) Field of Classification Search
CPC ..... A61B 5/126; A61B 5/7214; A61B 5/7257; A61B 5/0066; A61B 5/0051; G01B 9/02091
See application file for complete search history.

(56) References Cited

U.S. PATENT DOCUMENTS 10,072,920 B2 * 9/2018 Adie ................... A61B 5/0066
10,197,379 B2 * 2/2019 Adie ................... G01B 9/02091
(Continued)

FOREIGN PATENT DOCUMENTS

WO     2017063090 A1    4/2017

OTHER PUBLICATIONS

International Search Report of the parent PCT application PCT/CA2018/050200 dated Jul. 3, 2018.

(Continued)

*Primary Examiner* — Sanjay Cattungal
(74) *Attorney, Agent, or Firm* — Hill & Schumacher (57) ABSTRACT

Systems and methods are provided for performing phase-sensitive optical coherence tomographic (PS-OCT) measurements involving the vibrographic response of an acoustic stimulus. Detected signals are processed to provide sampled time-dependent vibrographic data characterizing a vibratory amplitude and phase response over one or more periods of the acoustic stimulus. The sampled time-dependent vibrographic data is processed to suppress the sinusoidal signal component associated with the acoustic stimulus, thereby providing a residual data associated with noise. The residual data is processed to obtain an estimate of the motion noise, and the motion noise is subtracted from the sampled time-dependent vibrographic data in order to provide noise-corrected vibrographic data. The noise-corrected vibrographic data can be processed to obtain one or more vibrographic measures and/or one or more images.

28 Claims, 5 Drawing Sheets

(52) U.S. Cl.
CPC .......... *A61B 5/7214* (2013.01); *A61B 5/7257* (2013.01); *G01B 9/02091* (2013.01)

(56) References Cited

U.S. PATENT DOCUMENTS

| | | | |
|---|---|---|---|
| 2009/0296102 A1* | 12/2009 | Tamura | A61B 5/0066 356/512 |
| 2011/0174078 A1* | 7/2011 | Chinn | G01H 9/004 73/657 |
| 2013/0060131 A1* | 3/2013 | Oghalai | A61B 1/00165 600/425 |
| 2014/0187904 A1* | 7/2014 | Razani | A61B 5/0066 600/407 |
| 2015/0148654 A1* | 5/2015 | Whanwook | A61B 3/102 600/407 |
| 2015/0204651 A1* | 7/2015 | Yuan | G01B 9/02075 356/479 |
| 2015/0305622 A1* | 10/2015 | Hogan | A61B 5/0066 600/425 |

* cited by examiner

SYSTEMS AND METHODS FOR PERFORMING PHASE-SENSITIVE ACOUSTIC VIBRATIONS USING OPTICAL COHERENCE TOMOGRAPHY

CROSS-REFERENCE TO RELATED APPLICATION

This application is a National Phase application claiming the benefit of the international PCT Patent Application No. PCT/CA2018/050200, filed on Feb. 22, 2018, in English, which claims priority to U.S. Provisional Application No. 62/463,298, titled "SYSTEMS AND METHODS FOR PERFORMING PHASE-SENSITIVE ACOUSTIC VIBRATIONS USING OPTICAL COHERENCE TOMOGRAPHY" and filed on Feb. 24, 2017, the entire contents of which are incorporated herein by reference.

BACKGROUND

The present disclosure relates to the use of optical coherence tomography for the phase-sensitive detection of an acoustic vibrations. In particular, the present disclosure relates to phase-sensitive optical coherence tomographic vibrography and optical coherence tomographic elastography.

In phase-sensitive optical coherence tomographic (PS-OCT) vibrography, the sinusoidal motion of a structure located at a particular pixel in the image produces a sinusoidal phase variation between successive A-lines produced by taking the discrete Fourier transform (DFT) of the sampled interferogram (in swept-source OCT) and the sampled spectrum (in spectral domain OCT). In the absence of noise, the measured phase at each vibrating pixel is characterized by a sinusoid.

In real systems, however, there are two major sources of noise that contaminate the signal. First, random broadband noise due to shot noise and residual intensity noise is present in the passband and must be averaged down to an acceptably low level in order to recover the vibratory response. Second, motion noise caused by motion of the subject relative to the OCT optics caused, for example, by breathing and heartbeat, produce very large amplitude and low frequency phase noise that dwarfs the vibrations of interest. For example, in the case of middle ear imaging, the head moves about a millimeter every time the heart beats, but the vibration of the middle ear structures in response to sound are as low as a few nanometers—hundreds of thousands times smaller. Such motion noise presents challenges in signal processing, often leading to very long signal acquisition times that conflict with clinical requirements.

SUMMARY

Systems and methods are provided for performing phase-sensitive optical coherence tomographic (PS-OCT) measurements involving the vibrographic response of an acoustic stimulus. Detected signals are processed to provide sampled time-dependent vibrographic data characterizing a vibratory amplitude and phase response over one or more periods of the acoustic stimulus. The sampled time-dependent vibrographic data is processed to suppress the sinusoidal signal component associated with the acoustic stimulus, thereby providing a residual data associated with noise. The residual data is processed to obtain an estimate of the motion noise, and the motion noise is subtracted from the sampled time-dependent vibrographic data in order to provide noise-corrected vibrographic data. The noise-corrected vibrographic data can be processed to obtain one or more vibrographic measures and/or one or more images.

Accordingly, in a first aspect, there is provided a method of performing phase-sensitive optical coherence tomographic detection of a vibrographic response to an acoustic stimulus, the method comprising:
  applying an acoustic stimulus at a known frequency and performing phase-sensitive optical coherence tomographic measurements to obtain a set of interferograms;
  performing discrete Fourier transforms on the interferograms to obtain sampled time-dependent vibrographic data characterizing a vibratory amplitude and phase response due to the acoustic stimulus;
  adding two or more time-shifted portions of the sampled time-dependent vibrographic data to suppress a sinusoidal response associated with the acoustic stimulus, thereby obtaining residual data comprising noise;
  processing the residual data to obtain an estimate of motion noise;
  subtracting the estimated motion noise from the sampled vibrographic data to obtain noise-corrected vibratory response data; and
  processing the noise-corrected vibratory response data to generate one or more vibrographic measures.

In another aspect, there is provided a system for performing phase-sensitive optical coherence tomographic detection of a vibrographic response to an acoustic stimulus, the system comprising:
  a phase-sensitive optical coherence tomography system comprising a swept-source laser and an optical scanning subsystem;
  an acoustic stimulus source; and
  control and processing circuitry operably connected to the phase-sensitive optical coherence tomography system and the acoustic stimulus source, the control and processing circuitry comprising a processor and a memory, wherein the processor is configured to execute instructions stored in said memory for performing the steps of:
    controlling the acoustic stimulus source to apply an acoustic stimulus at a known frequency and employing the phase-sensitive optical coherence tomography system to perform phase-sensitive optical coherence tomographic measurements to obtain a set of interferograms;
    performing discrete Fourier transforms on the interferograms to obtain sampled time-dependent vibrographic data characterizing a vibratory amplitude and phase response due to the acoustic stimulus;
    adding two or more time-shifted portions of the sampled time-dependent vibrographic data to suppress a sinusoidal response associated with the acoustic stimulus, thereby obtaining residual data comprising noise;
    processing the residual data to obtain an estimate of motion noise;
    subtracting the estimated motion noise from the sampled vibrographic data to obtain noise-corrected vibratory response data; and
    processing the noise-corrected vibratory response data to generate one or more vibrographic measures.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 4A-B show the measured noise floor in the absence of an acoustic stimulus for a 256-line image for real-time OCT Doppler data obtained based on measurements performed on the middle ear.

FIGS. 4C-E show a 256(w)×300(d) image of a middle ear being excited with a 98 dB SPL tone collected at a line rate of 6.4 lines per second (40 s for the image). FIG. 4C shows the vibration data over a 0-180 nm display range, while

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present disclosure provides systems and methods for performing phase-sensitive optical coherence tomographic (PS-OCT) detection and signal of acoustic vibrations, where the detected signals are processed such that motion noise is suppressed or reduced, thereby allowing an improved vibratory signal-to-noise ratio to be achieved with less averaging than conventional methods.

Figure 1:
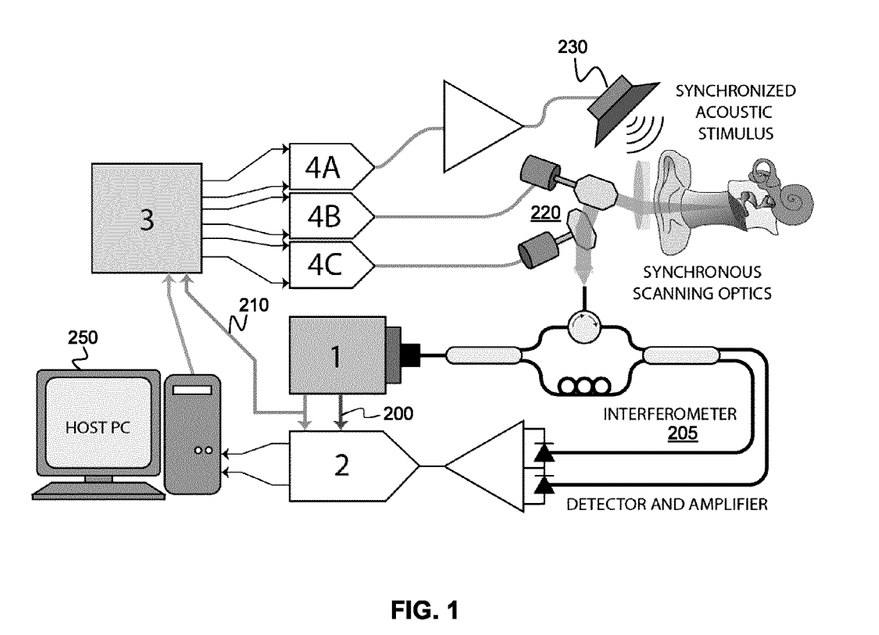
FIG. 1 shows an example system for performing PS-OCT vibrography.

Referring to FIG. 1, an example system is shown for performing PS-OCT vibrography measurements. It is noted that this system provides but one example system for performing PC-OCT measurements, and that other systems, such as a Fourier-domain PS-OCT system of any topology, could be used as platform to perform the phase measurements and motion noise suppression techniques described below. This example system shown in FIG. 1 is described in International Patent Application No. PCT/CA2016/051199, titled "SYSTEMS AND METHODS FOR SWEPT SOURCE OPTICAL COHERENCE TOMOGRAPHIC VIBROGRAPHY" and filed on Oct. 14, 2016, which is incorporated herein by reference in its entirety. The example OCT vibrography system shown in FIG. 1 employs a swept-source akinetic laser 1, such as the SLE-101E akinetic laser from Insight Photonics Solutions, which provides a sweep frequency of 100 kHz and a fiber-based interferometer 205. The swept source laser 1 provides a sample clock 200 and a sweep trigger 210, where the sweep trigger 210 signals the beginning of each new laser sweep (each A-scan event corresponding to an acquired interferogram). The sweep trigger 210 may be derived from the sample clock 200. The sample clock 200 and sweep trigger 210 supply timing signals to other clocked and temporally synchronized components of the OCT vibrography system. In the present example embodiment, the akinetic laser thus acts as the timing master to other system components, which themselves act as timing-slaves.

The sample clock 200 and the sweep trigger 210 are provided to the data acquisition card 2 (e.g., ATS9351, 12-bit, 500 MHz PCIE digitizer, Alazar Technologies) to synchronize laser sweeping and data acquisition. The sweep trigger 210 is also used to clock internal functions of a field-programmable-gate-array 3 (e.g., MachXO2-7000HE, Lattice Semiconductor) that, through digital-to-analog converters 4 (DAC), respectively control the scanning optics 220 and the acoustic stimulus source 230 that generates an acoustic stimulus signal for excitation of the object of interest, such as structures within the middle ear.

A digital synthesis approach may be employed to generate the scanning signals and acoustic signals. In the example implementation shown in FIG. 1, a computer 250 is employed to send control signals to components of the system, but the synchronization the optical beam scanning and the phase of the acoustic stimulus is determined by the sweep trigger.

The use of the single clock generated by the akinetic laser to synchronize the scanning subsystem 220 and the acoustic stimulus source 230 provides the advantage of synchronously controlling the phase of the acoustic stimulus during optical scanning. In the present example embodiment shown in FIG. 1, a synchronized acoustic stimulus signal is generated by the FPGA by incrementing a counter on the rising edge of each clock cycle (i.e., on each laser sweep). This counter acts as a phase accumulator and is used to step though a lookup table containing the values of a sinusoid of a particular acoustic frequency. On each clock edge, the FPGA updates the value of a digital-to-analog converter 4A (e.g., DAC900E, Texas Instruments) that drives an audio amplifier and speaker used to excite vibrations in the sample.

Two synchronized lateral digital scanning signals (one for horizontal scanning, and one for vertical scanning) are also generated by the FPGA by incrementing a counter on the rising edge of the each laser sweep clock cycle (i.e. in order to count laser sweeps). Once the desired number of laser sweeps for a particular scan configuration (image line) have completed, the scan mirror position is incremented by a chosen step size and the laser sweep counting starts over. This process is repeated once for every line in the image. Once the desired number of steps have been made (i.e. the number of lines in the image), the signal is reset to a chosen initial value and the lateral scan procedure starts over. The FPGA updates the values of two digital-to-analog converters 4B and 4C (e.g., DAC900E, Texas Instruments) that respectively trigger mirror drivers (shown as cylinders in FIG. 1) to drive the horizontal and vertical scanning optics/mirrors (shown as polygons in FIG. 1, mounted to their respective driver). In one example embodiment, there are two mirror drivers, each of which drive a mirror. While FIG. 1 shows a mirror-based scanning subsystem 220, in other example embodiments, one or more of the mirrors may be replaced by other scanning elements. Non-limiting examples of non-mirror based scanning elements include acousto-optic deflectors, electro-optic deflectors, liquid crystal spatial light modulators, and photorefractive scanners.

In the example system shown in FIG. 1, the acoustic excitation remains phase-locked to the laser sweeps via the sweep trigger, and the accumulation of acoustic phase during and between consecutive image frames can be controlled and predicted deterministically. Without such phase-locking, even relatively slow-phase drifts between the acoustic stimulus and the laser sweeping would tend to average away the vibrational information. It is the synchronization of the timing components to the akinetic laser clock that allows this simple form of indexing to track acoustic phase changes, and makes the processing steps well suited to parallel processing on graphical processing units (GPUs) using, for instance, the Compute Unified Device Architecture (CUDA) framework.

The example system shown in FIG. 1, and the example methods of signal processing described in detail below, are well suited when using akinetic lasers because of the characteristic way that linear sweeping over a broad bandwidth is achieved: through controlled mode-hopping in the akinetic swept-source architecture. The laser executes linear-in-frequency sweeps over a limited frequency range. When the end of that range is reached the laser undergoes a mode-hopping event. During this event the interferogram data is invalid and must be removed prior to line reconstruction. Fortunately, the mode hops are repeatable and deterministic across sweeps, such that, for a given laser calibration and set of sweep settings, the invalid data can be identified. However, the presence of these invalid points and their dependence on calibration and sweep parameters means that a system synchronized to the laser sampling clock (or the "k-clock" in the language conventionally used for swept source lasers) results in a phase error that depends on the sweep settings and calibration. In an example embodiment, synchronizing to the start of the sweep with an external FPGA avoids this phase error.

The system shown in FIG. 1, and other PS-OCT vibrography systems, may be employed for otological vibrographic measurements. When an acoustic tone is presented to the ear, the middle ear structures (the eardrum and ossicles) are set into periodic motion at the acoustic frequency as they conduct sound energy to the inner ear. When the vibrating structures are imaged with PS-SS-OCT, phase variations in the interferometric signal appear at the acoustic frequency as well. While the audible range of acoustic frequencies is typically cited as 20 Hz-20 kHz, the range of diagnostically useful frequencies is limited to 100 Hz to 10 kHz.

As described above, vibrography data is obtained from a PS-OCT vibrography system by processing multiple interferograms for each A-line and extracting the amplitude and phase behaviour of the structure, in response to the acoustic stimulus, from the interferograms. A discrete Fourier transform (DFT) is obtained for each sampled interferogram (in swept-source OCT) or sampled spectrum (in spectral domain OCT), yielding, for each pixel associated with a given structure, a signal characterized by a phase that evolves as a sinusoid having the same frequency as the acoustic stimulus.

In real systems, however, additional error sources add noise to the sinusoidal response associated with the vibration of the structure that is induced by the acoustic stimulus. For example, there are two major sources of noise that contaminate the signal. A first source of noise is random broadband noise due to shot noise, residual intensity noise and other random sources that overlaps the measurement passband and must be averaged down to an acceptably low level in order to recover the vibratory response. A second source of noise is motion noise that is generated by motion of the subject relative to the OCT optics. Such motion noise can be caused, for example, by breathing and heartbeat, which can produce very large amplitude and low frequency phase noise that dwarfs the vibrations of interest. As noted above, in the case of middle ear imaging, the head moves about a millimeter every time the heart beats, but the vibration of the middle ear structures in response to sound are as low as a few nanometers—hundreds of thousands times smaller.

Unfortunately, motion noise, which is non-sinusoidal, cannot be aligned with the sampling window in such a way as to be isolated in small number of DFT bins due to a "spectral splatter" effect. Furthermore, conventional windowing (i.e. multiplication by a Hanning window) along with averaging is ineffective at removing such a large signal, requiring extremely long DFT lengths (or long temporal averaging of many short duration DFTs). Temporal averaging for more than a minute is impractical in a clinical scenario since patients are generally not able to keep still long enough to reach the desired sensitivity.

In various example embodiments of the present disclosure, PS-OCT signals are processed using methods that take advantage of the low-frequency nature of motion noise, relative to the acoustic frequency variations of interest, in order to achieve noise suppression. For example, heartbeat noise has little spectral content above 100 Hz, whereas clinically relevant acoustic measurements typically lie at frequencies above 500 Hz. Motion noise suppression may be achieved by combining different portions of a detected vibrographic response in order to suppress the contribution of the sinusoidal component associated with the acoustic stimulus, thereby leaving a residual signal associated with noise. This residual signal can be processed to obtain an estimate of motion noise, which can in turn be subtracted from the vibrographic signal to achieve motion noise suppression. The following section of the present disclosure describes an example method of motion noise suppression, in the example context of PS-OCT vibrography measurements.

After performing a DFT on each interferogram for a given A-line, the signal at a given pixel, will take the form:

$$x[n] = A\cos\left(\frac{2\pi Kn}{N} + \theta\right) + y[n],$$

where A and θ are the amplitude and phase of the sinusoid of interest, and y[n] contains all other contributions to the measured signal, including phase drifts and all noise sources, and N phase samples are obtained for K periods of the sinusoid of interest. For the simple case where K is an integer, The DFT of x[n] is given by $$X[k] = \sum_{n=0}^{N-1} x[n]e^{-\frac{j2\pi kn}{N}},$$

$$X[k] = \frac{AN}{2}e^{j\theta}(\delta[k-K] + \delta[k+K]) + Y[k],$$

where δ[k] is a delta function, and Y[k] is the DFT of y[n]. Here Y[k] can be understood as corrupting the measurement of $$\frac{AN}{2}e^{j\theta},$$

which is the information of interest.

In one example implementation, if instead of performing an N-point DFT, two separate DFTs, each using M=N−N/2K points, are performed on the first M samples and last M samples of the data, respectively, then one obtains:

$$X_1[k] = \sum_{n=0}^{M-1}\left(A\cos\left(\frac{2\pi Kn}{N} + \theta\right) + y[n]\right)e^{-\frac{j2\pi kn}{M}}, \text{ and}$$

$$X_2[k] = \sum_{n=0}^{M-1}\left(A\cos\left(\frac{2\pi K(n+N/2K)}{N} + \theta\right) + y[n+N/2K]\right)e^{-\frac{j2\pi kn}{M}}$$

where $X_1[k]$ and $X_2[k]$ are the DFTs of the first M and last M samples of x[n], respectively. The following equality exists:

$$A\cos\left(\frac{2\pi K(n+N/2K)}{N} + \theta\right) = A\cos\left(\frac{2\pi Kn}{N} + \pi + \theta\right) = -A\cos\left(\frac{2\pi Kn}{N} + \theta\right)$$

The sum of $X_1[k]$ and $X_2[k]$ then gives:

$$X'[k] = X_1[k] + X_2[k] = \sum_{n=0}^{M-1}(y[n] + y[n+N/2K])e^{-\frac{j2\pi kn}{M}}$$

which provides a signal which only depends on y[n], since the shift in n by N/2K samples produces cancellation of the signal of interest corresponds to a shift of exactly one half period of the sinusoid of interest.

The same effect could be achieved by shifting by any odd multiple of half periods, with M=N−N(2p+1)/2K for p in N. Here, only the case where p=0 is considered because it produces the greatest overlap between $x_1[n]$ and $x_2[n]$ and is the simplest case.

It is noted that the present example method could be performed in the time domain, as opposed to the frequency domain. For example, the calculation of X'[k] could be carried out in the time domain without transforming into the frequency domain by calculating:

$$x'[n] = x_1[n] + x_2[n] = y[n] + y[n+N_{2K}],$$

where n ranges between 0 and M (i.e. N−N/2K). This method can be useful to reduce computational complexity if only a subset of the frequency domain is of interest and the entire DFT is not required, as in the current application where only the DFT coefficient at k=±K is of interest.

A number of possible approaches could then be applied to reject the unwanted contributions of y[n] to X[k]. To do so, an estimate of y[n] or Y[k] is first obtained from X'[k] or from x'[n]. One can take advantage of the fact that if the time-varying component of y[n] in $x_1[n]$ is equal to the time varying component of y[n] in $x_2[n]$, then the time-varying component of x'[n] will simply be equal to 2y[n] from n=0 to n=M. It is these common components that are most readily compensated out. Some non-limiting examples of approaches that could be applied are provided below.

In a first example method, X'[k] could be appropriately scaled and zero padded up to N samples and inverse transformed to the time domain as an interpolation step, or interpolated by any other conventional means, to provide a direct estimate of y[n] from n=0 to n=N that can be subtracted from x[n] for a noise corrected version of the data.

In a second example method, a Taylor series representations of x'[n] could be made, taking the form of a series of noise coefficients corresponding to each of the Taylor terms. Since each of these terms produce easily calculated effects on X[k], their contributions can be removed.

In a third example method, any other noise model containing a parametric expression for the noise could be fit to using, for instance, least squares fitting to estimate a set of parameters that describe the noise and so that their contributions can be removed from the measurement.

In the preceding example embodiment, two time-shifted PS-OCT signals (after having performed a DFT on the interferogram data) are added in order to remove the contribution of the primary sinusoidal component that is associated with the acoustic stimulus. However, it will be understood that that the method described above, where two portions of the sampled data are shifted by any odd multiple of half periods, with M=N−N(2p+1)/2K for p in N, is but one example method that achieves cancellation of the sinusoidal component, and that other methods, in which one or more portions of the sampled data are added to achieve such cancellation, may be employed in the alternative.

Figure 2:
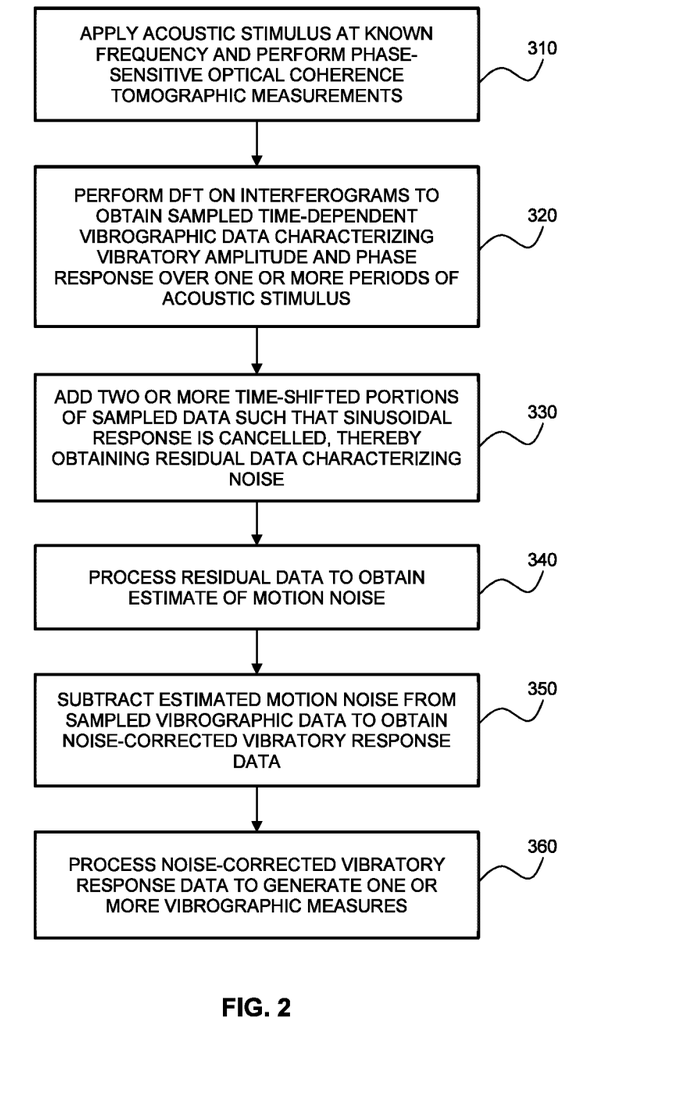
FIG. 2 shows an example method for performing PS-OCT measurements of acoustic vibrations with reduced susceptibility to low-frequency motion noise.

Referring now to FIG. 2, a flow chart is provided that illustrates an example method of reducing or suppressing motion noise from PS-OCT measurements of a vibratory response to an acoustic stimulus. As shown at 310, an acoustic stimulus is applied at a known frequency, phase-sensitive optical coherence tomographic measurements are performed (for example, using the system and optionally the methods described in International Patent Application No. PCT/CA2016/051199). At step 320, DFTs are performed on the measured interferograms, to obtain sampled time-dependent vibrographic data characterizing the vibratory amplitude and phase response over one or more periods of acoustic stimulus. The resulting sampled vibrographic data is then processed, as shown at step 330, by adding two or more time-shifted portions of sampled data, such that sinusoidal response associated with the acoustic stimulus is cancelled, thereby obtaining residual data characterizing the noise. The residual data is then processed to obtain estimate of motion noise, as shown at step 340. For example, the methods described above may be used, such as using a Taylor series approximation with one or more terms to extract an estimate of one or more parameters characterizing the motion noise. The estimated motion noise is then subtracted from the sampled vibrographic data to obtain noise-corrected vibratory response data. The noise-corrected vibratory response data is then processed to generate one or more vibrographic measures, as shown at step 360. In some example implementations, the one or more vibrographic measures may be employed to generate one or more images. This example method can be performed by any suitable processing circuitry, such as the FPGA 3 or the computer 250 shown in FIG. 1.

An example of an approach to remove the noise component is shown below. If the noise $y[n]$ can be assumed to be very low in frequency on the timescale of the acoustic period, the noise can be approximated as an additive linear ramp in time with an unknown slope, and can be described by $$y[n]=mn,$$

which is effectively a first-order approximation to the Taylor series method described above. Again assuming the simple case where K is an integer, The DFT of the measured sequence is given by the expression:

$$X[k] = \frac{AN}{2}e^{j\theta}(\delta[k-K]+\delta[k+K]) - m\frac{N}{1-e^{-\frac{j2\pi k}{N}}}.$$

Here, the second term shows how the background ramp noise contaminates the measurement. Calculating $x_1[n]+x_2[n]$ an alternate sequence is given by:

$$x'[n]=x_1[n]+x_2[n]=2mn+mN/2,$$

which is a straight line with a slope equal to twice that of $y[n]$, giving an indirect measure of the noise component. By performing a linear regression on this alternate sequence $x'[n]$, an estimate of the slope m can be made by:

$$\bar{m} = \frac{1}{2}\frac{N'\sum_n x'[n]n - \sum_n x'[n]\sum_n n}{N'\sum_n n^2 - \{\sum_n n\}^2},$$

where N' is the number of points in $x'[n]$ contributing to the estimate (which is not necessarily equal to N). Finally, an estimate $\overline{X[k]}$ can be made of the noise corrected version of $X[k]$ by calculating $$\overline{X[k]} = X[k] - \left(-\bar{m}\frac{N}{1-e^{-\frac{j2\pi k}{N}}}\right) =$$
$$\frac{AN}{2}e^{j\theta}(\delta[k-K]+\delta[k+K]) + (\bar{m}-m)\frac{N}{1-e^{-\frac{j2\pi k}{N}}},$$

which can be thought of as a subtraction of the straight-line components contribution to the DFT of the measured signal, and clearly shows that a good estimate is achieved when $\bar{m}$ approaches m.

Figure 3:
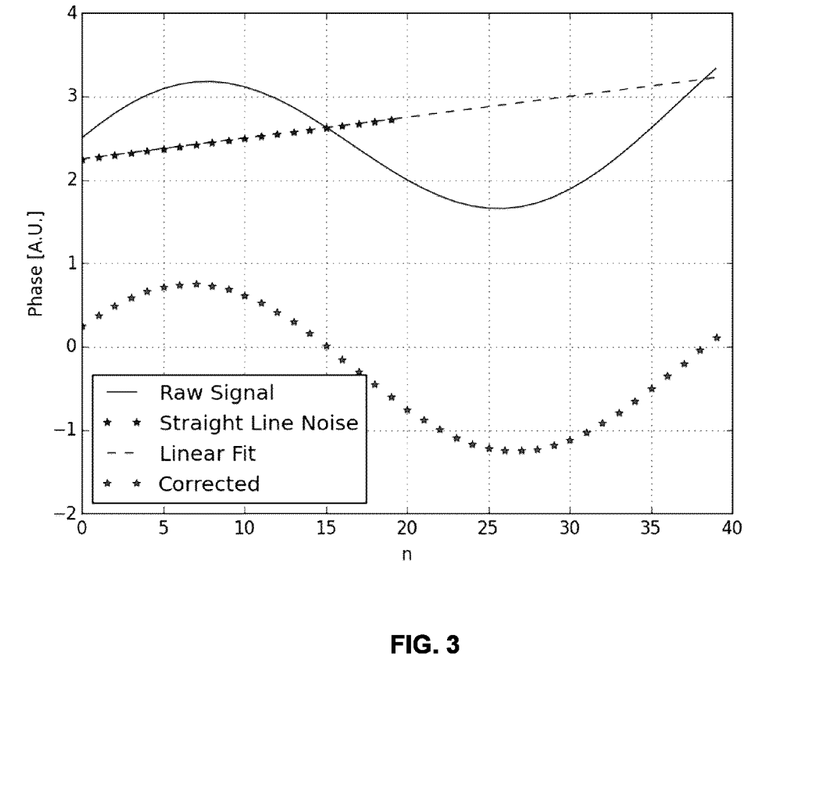
FIG. 3 shows a plot demonstrating the successful removal of low-frequency motion noise (characterized by a slope) from PS-OCT vibrography data.

An example is shown in the FIG. 3, where a raw signal, $\phi[n]$ (solid blue), contains a sinusoid of interest riding on an offset and linear ramp noise component. The sequence is N=40 samples long, and the frequency bin of interest is k=1 since the period of the sinusoid is also 40 samples. The calculated sequence x'[n] (blue stars) is used to extract the slope of the background noise using a least square fit (dashed blue) which is then subtracted away from x[n] to give a corrected sequence that approximates the sinusoidal component (green stars) with no straight-line background noise. The ideal value of the DFT at k=1 for the sinusoidal component is $X[1]=20.0000e^{-j1.0472}$. With no noise correction, the value of the DFT for x[n] is computed to be $X[1]=14.509e^{-j0.8570}$. However, after applying the noise correction, a very accurate estimate is obtained with $\overline{X[1]}=20.0000e^{-j1.0472}$.

These same techniques can be applied to any system that is meant to measure the periodic vibration of structures in response to a periodic drive using OCT in the presence of low-frequency noise sources. One application that could benefit from this technique is OCT elastography. In OCT elastography tissue is mechanically vibrated using a variety of techniques including contact force, ultrasound acoustic radiation force, laser heating, microwave heating and delivery of sound. The tissues vibrational response to this stimulus it then measured by tracking the phase of the OCT signal just in the case of Doppler vibrography. The ratio of the tissue's vibration to the strength of the driving force provides a measure of the tissue's elasticity which is important for distinguishing and classifying tissue types and assessing states of disease. For instance, many tumours affect tissue elasticity and so OCT elastography can be used to detect them. For cases where elastography is performed in vivo, the techniques presented here for removing artefacts associated with patient motion would be equally applicable and could be used to improve frame rates, sensitivity, signal-to-noise ratio or some combination of these.

EXAMPLES

The following examples are presented to enable those skilled in the art to understand and to practice embodiments of the present disclosure. They should not be considered as a limitation on the scope of the disclosure, but merely as being illustrative and representative thereof.

Figure 4A:
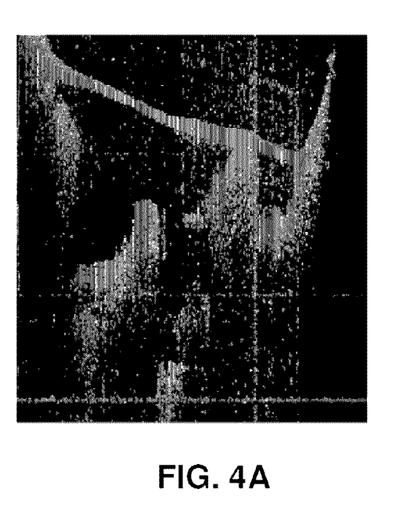
FIG. 4A shows the noise floor obtained in the absence of motion noise reduction.
Figure 4B:
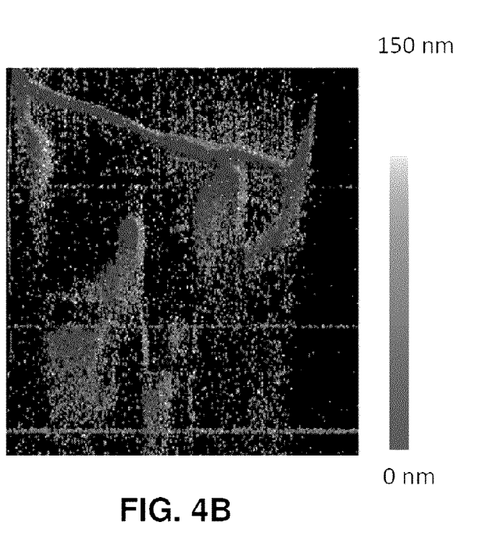
FIG. 4B shows the noise floor obtained in after performing motion noise reduction.

The technique was implemented in the numerical computing library CUDA and applied to real-time OCT Doppler data acquisition of the middle ear. FIGS. 4A and 4B show the measured noise floor in the absence of an acoustic stimulus for a 256-line image. FIG. 4A shows the noise floor level obtained from the DFT of the phase and without applying the motion noise reduction technique. FIG. 4B shows the same ear with the motion noise reduction technique applied. Both images were measured in 40 seconds (6.4 lines/s). As can be seen, the technique results in a roughly 30-fold improvement in the measured noise floor, bringing it from around 70 nm to just a few nanometers.

Figure 4C:
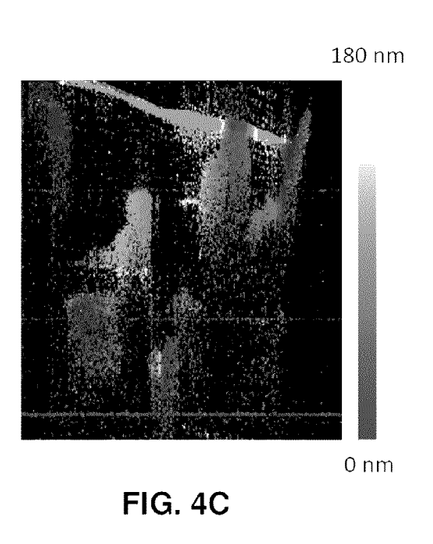
Figure 4D:
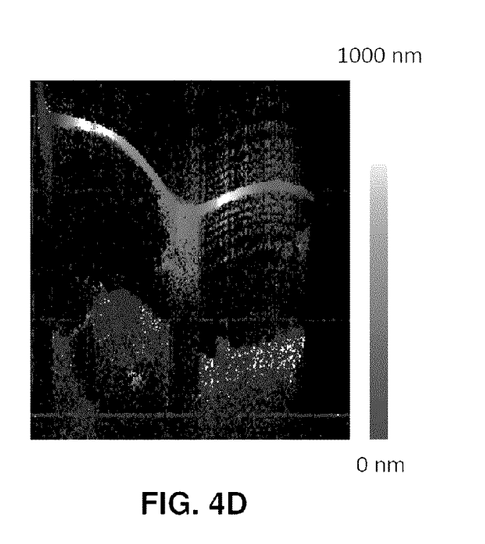
FIG. 4D shows the vibration data over a 0-1000 nm range.

When an acoustic stimulus is applied, this technique allows the vibratory response of every pixel in a 256(w)× 300(d) pixel frame to be measured with excellent SNR with less than a minute. FIGS. 4C and 4D show a 256(w)×300(d) image of a middle ear being excited with a 98 dB SPL tone collected at a line rate of 6.4 lines per second (40 s for the image). FIG. 4C shows the vibration data over a 0-180 nm display range and FIG. 4D shows the vibration data over a 0-1000 nm range.

Figure 4E:
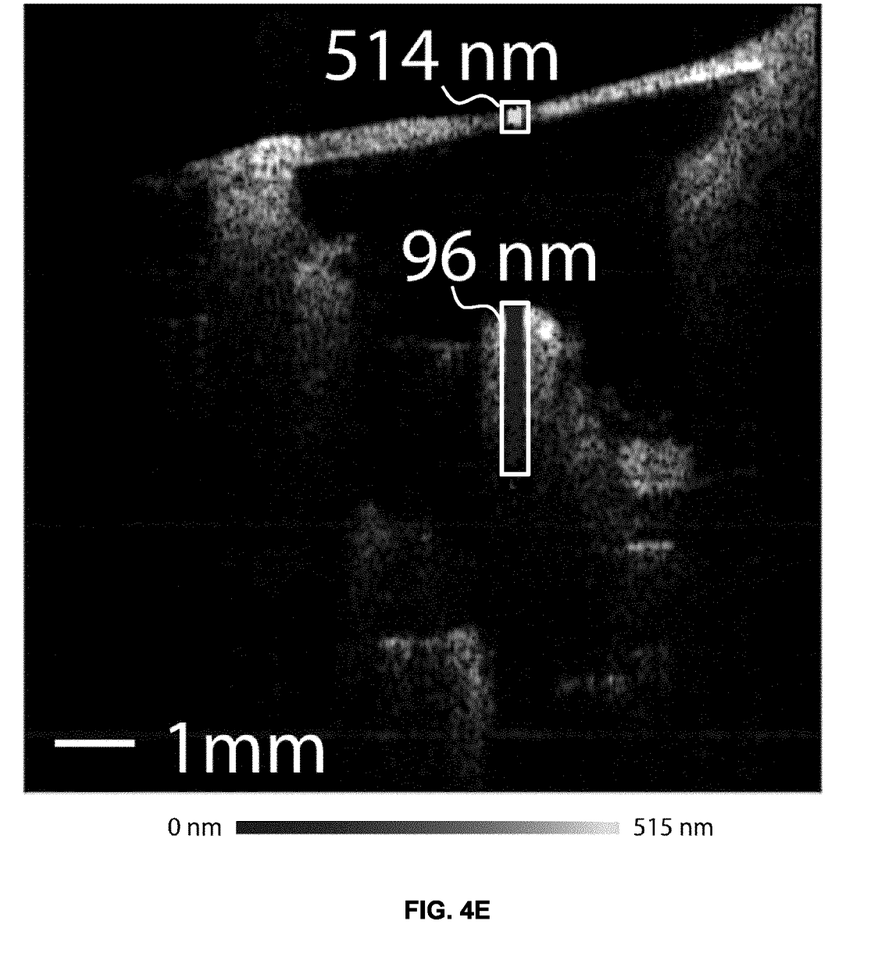
FIG. 4E shows an image obtained without the motion noise rejection, in which Doppler data for a single image line, acquired over a 5 s duration, is shown.

In comparison, without the motion noise rejection, 5 s of acquisition time is required per line to obtain a similar vibratory noise floor as shown in FIG. 4E. The motion rejection technique therefore enables a 32-fold increase in acquisition speed in PS-OCT vibrometry.

Therefore what is claimed is:

1. A method of performing phase-sensitive optical coherence tomographic detection of a vibrographic response to an acoustic stimulus, the method comprising:
   applying an acoustic stimulus at a known frequency and performing phase-sensitive optical coherence tomographic measurements to obtain a set of interferograms;
   performing discrete Fourier transforms on the interferograms to obtain sampled time-dependent vibrographic data characterizing a vibratory amplitude and phase response due to the acoustic stimulus;
   adding two or more time-shifted portions of the sampled time-dependent vibrographic data to suppress a sinusoidal response associated with the acoustic stimulus, thereby obtaining residual data comprising noise;
   processing the residual data to obtain an estimate of motion noise;
   subtracting the estimated motion noise from the sampled vibrographic data to obtain noise-corrected vibratory response data; and
   processing the noise-corrected vibratory response data to generate one or more vibrographic measures.

2. The method according to claim 1 wherein the two or more time-shifted portions are added by adding a first portion of the sampled time-dependent vibrographic data to a second portion of the sampled time-dependent vibrographic data, wherein the first portion and the second portion are selected to cancel the sinusoidal response associated with the acoustic stimulus.

3. The method according to claim 2 wherein the first portion and the second portion partially overlap.

4. The method according to claim 2 wherein the sampled time-dependent vibrographic data characterizing a vibratory amplitude and phase response includes samples spanning an integer number of periods of the acoustic stimulus.

5. The method according to claim 2 wherein the sampled time-dependent vibrographic data characterizing a vibratory amplitude and phase response includes samples spanning a non-integer number of periods of the acoustic stimulus.

6. The method according to claim 4 wherein the first portion includes the first $(N-N(2p+1))/2K$ samples, and the second portion includes the last $(N-N(2p+1))/2K$ samples, wherein N is the total number of samples in the one or more periods, K is the number of periods, and p is a whole number.

7. The method according to claim 4 wherein the first portion includes the first $N-N/(2K)$ samples, and the second portion includes the last $N-N/(2K)$ samples, wherein N is the total number of samples in the one or more periods, and K is the number of periods.

8. The method according to claim 1 wherein the residual data is obtained after having applied a discrete Fourier transform to the sampled time-dependent vibrographic data, and wherein the residual data is processed by padding the residual data with a suitable number of zeros and performing an inverse transform to obtain a time domain result, and processing the time domain result to obtain the estimate of the motion noise.

9. The method according to claim 1 wherein the residual data is processed by fitting a noise component of the time-dependent vibrographic data to one or more terms of a Taylor series.

10. The method according to claim 1 wherein the residual data is processed by fitting a noise component of the time-dependent vibrographic data according to a parametric functional form.

11. The method according to claim 1 wherein the residual data is processed by fitting a noise component of the time-dependent vibrographic data to a linear function.

12. The method according to claim 1 wherein the two or more time-shifted portions are added after having performed a discrete Fourier transform on the sampled time-dependent vibrographic data.

13. The method according to claim 1 wherein the phase-sensitive optical coherence tomographic measurements are otological vibrographic measurements.

14. The method according to claim 1 wherein the phase-sensitive optical coherence tomographic measurements are phase-sensitive optical coherence tomography vibrography measurements.

15. The method according to claim 1 wherein the phase-sensitive optical coherence tomographic measurements are phase-sensitive optical coherence tomography elastography measurements.

16. The method according to claim 1 further comprising processing at least one of the one or more vibrographic measures to generate one or more images.

17. A system for performing phase-sensitive optical coherence tomographic detection of a vibrographic response to an acoustic stimulus, the system comprising:
   a phase-sensitive optical coherence tomography system comprising a swept-source laser and an optical scanning subsystem;
   an acoustic stimulus source; and
   control and processing circuitry operably connected to the phase-sensitive optical coherence tomography system and the acoustic stimulus source, the control and processing circuitry comprising a processor and a memory, wherein the processor is configured to execute instructions stored in said memory for performing the steps of:
      controlling the acoustic stimulus source to apply an acoustic stimulus at a known frequency and employing the phase-sensitive optical coherence tomography system to perform phase-sensitive optical coherence tomographic measurements to obtain a set of interferograms;
      performing discrete Fourier transforms on the interferograms to obtain sampled time-dependent vibrographic data characterizing a vibratory amplitude and phase response due to the acoustic stimulus;
      adding two or more time-shifted portions of the sampled time-dependent vibrographic data to suppress a sinusoidal response associated with the acoustic stimulus, thereby obtaining residual data comprising noise;
      processing the residual data to obtain an estimate of motion noise;
      subtracting the estimated motion noise from the sampled vibrographic data to obtain noise-corrected vibratory response data; and
      processing the noise-corrected vibratory response data to generate one or more vibrographic measures.

18. The system according to claim 17 wherein the control and processing circuitry is configured such that the two or more time-shifted portions are added by adding a first portion of the sampled time-dependent vibrographic data to a second portion of the sampled time-dependent vibrographic data, wherein the first portion and the second portion are selected to cancel the sinusoidal response associated with the acoustic stimulus.

19. The system according to claim 18 wherein the control and processing circuitry is configured such that the sampled time-dependent vibrographic data characterizing a vibratory amplitude and phase response includes samples spanning an integer number of periods of the acoustic stimulus.

20. The system according to claim 18 wherein the control and processing circuitry is configured such that the sampled time-dependent vibrographic data characterizing a vibratory amplitude and phase response includes samples spanning a non-integer number of periods of the acoustic stimulus.

21. The system according to claim 19 wherein the control and processing circuitry is configured such that the first portion includes the first $(N-N(2p+1))/2K$ samples, and the second portion includes the last $(N-N(2p+1))/2K$ samples, wherein N is the total number of samples in the one or more periods, K is the number of periods, and p is a whole number.

22. The system according to claim 19 wherein the control and processing circuitry is configured such that the first portion includes the first $N-N/(2K)$ samples, and the second portion includes the last $N-N/(2K)$ samples, wherein N is the total number of samples in the one or more periods, and K is the number of periods.

23. The system according to claim 17 wherein the control and processing circuitry is configured such that the residual data is obtained after having applied a discrete Fourier transform to the sampled time-dependent vibrographic data, and wherein the residual data is processed by padding the residual data with a suitable number of zeros and performing an inverse transform to obtain a time domain result, and processing the time domain result to obtain the estimate of the motion noise.

24. The system according to claim 17 wherein the control and processing circuitry is configured such that the residual data is processed by fitting a noise component of the time-dependent vibrographic data to one or more terms of a Taylor series.

25. The system according to claim 17 wherein the control and processing circuitry is configured such that the residual data is processed by fitting a noise component of the time-dependent vibrographic data according to a parametric functional form.

26. The system according to claim 17 wherein the control and processing circuitry is configured such that the residual data is processed by fitting a noise component of the time-dependent vibrographic data to a linear function.

27. The system according to claim 17 wherein the control and processing circuitry is configured such that the two or more time-shifted portions are added after having performed a discrete Fourier transform on the sampled time-dependent vibrographic data.

28. The system according to claim 17 wherein the control and processing circuitry is configured to further process at least one of the one or more vibrographic measures to generate one or more images.

* * * * *